(12) United States Patent
Woehr

(10) Patent No.: US 8,728,030 B2
(45) Date of Patent: May 20, 2014

(54) CATHETER DEVICE WITH NEEDLE GUARD

(75) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 35 days.

(21) Appl. No.: 13/381,842

(22) PCT Filed: Jul. 14, 2010

(86) PCT No.: PCT/EP2010/004298
§ 371 (c)(1),
(2), (4) Date: Feb. 6, 2012

(87) PCT Pub. No.: WO2011/006652
PCT Pub. Date: Jan. 20, 2011

(65) Prior Publication Data
US 2012/0123354 A1    May 17, 2012

(30) Foreign Application Priority Data

Jul. 15, 2009  (DE) .................... 20 2009 009 602 U

(51) Int. Cl.
*A61M 5/00* (2006.01)
*A61M 5/32* (2006.01)

(52) U.S. Cl.
USPC ........................... 604/111; 604/110; 604/272

(58) Field of Classification Search
USPC .................. 604/110, 111, 134, 272, 273
See application file for complete search history.

(56) References Cited

U.S. PATENT DOCUMENTS 5,755,709 A * 5/1998 Cuppy ..................... 604/164.12
6,921,391 B1    7/2005 Barker et al.

FOREIGN PATENT DOCUMENTS

EP    1 240 916 A1    9/2002

OTHER PUBLICATIONS

International Search Report completed Nov. 1, 2010 and mailed Nov. 8, 2010 from corresponding International Application No. PCT/EP2010/004298 filed Jul. 14, 2010 (7 pages).
Written Opinion completed Nov. 1, 2010 and mailed Nov. 8, 2010 from corresponding International Application No. PCT/EP2010/004298 filed Jul. 14, 2010 (7 pages).

* cited by examiner

*Primary Examiner* — Rebecca E Eisenberg
(74) *Attorney, Agent, or Firm* — Klein, O'Neil & Singh, LLP

(57) ABSTRACT

The present disclosure relates to a catheter device comprising a catheter hub in which a valve member is disposed, a needle fixed in a needle hub, the needle extending through the valve member in the catheter hub in a ready position, and a tubular receptacle in which the needle hub is displaceably guided and biased by a spring in a proximal direction relative to the receptacle, wherein the needle hub is releasably held in the ready position in the receptacle against the force of the spring by frictional force between needle circumference and catheter or catheter hub, which frictional force is reduced on retraction of the needle through the catheter hub such that the force of the spring prevails.

18 Claims, 3 Drawing Sheets

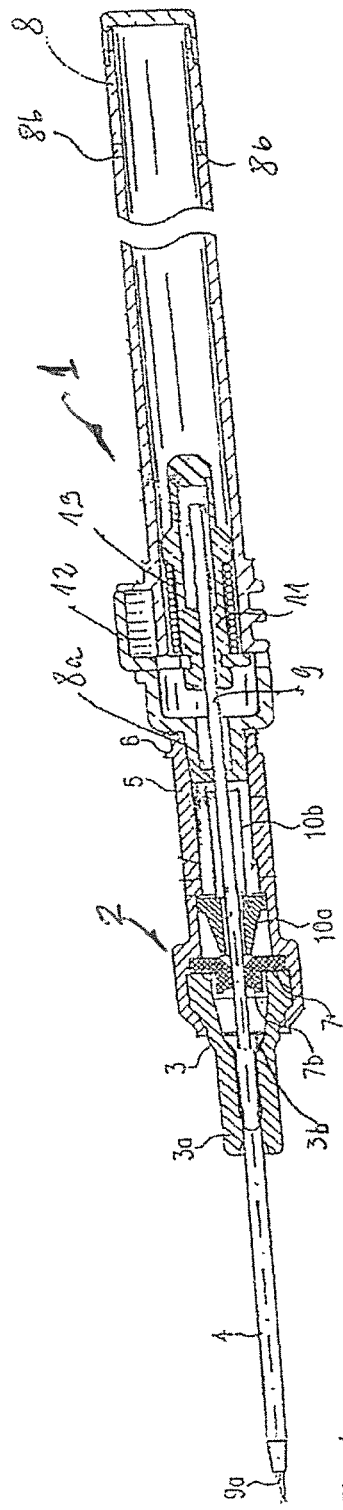
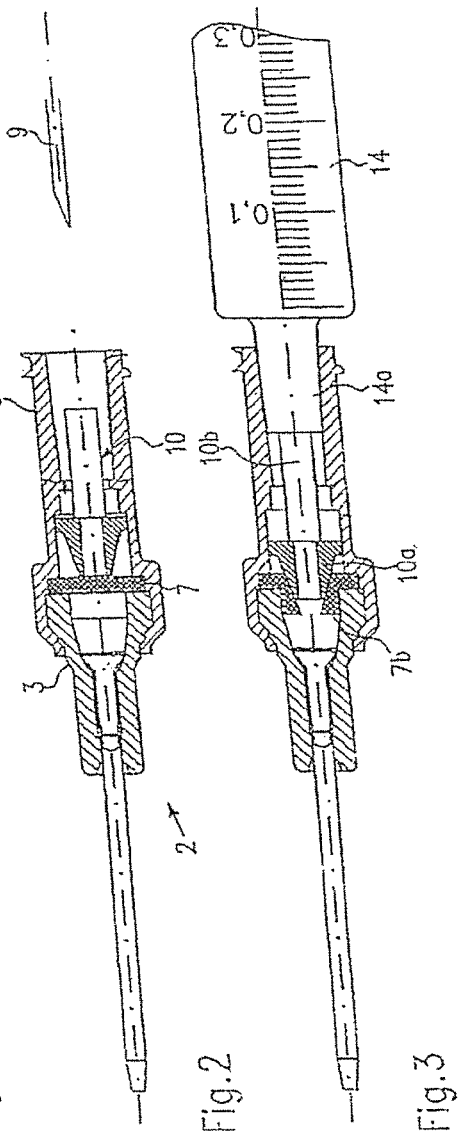
Fig.1　Fig.2　Fig.3

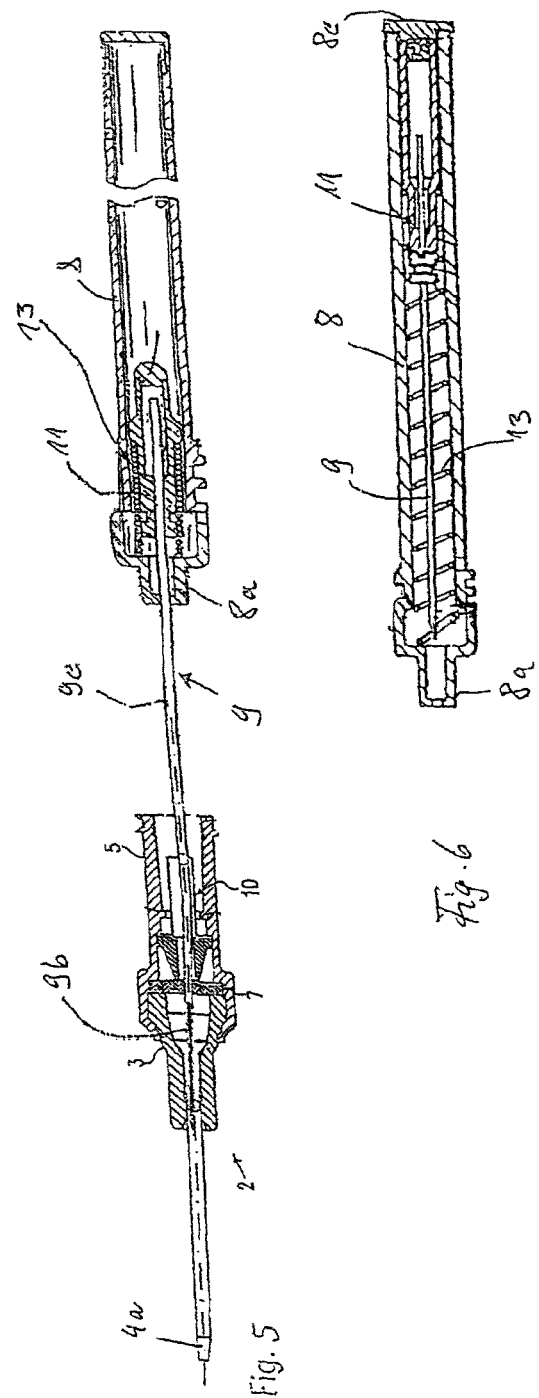

CATHETER DEVICE WITH NEEDLE GUARD

CROSS-REFERENCE TO RELATED APPLICATIONS

This is a national phase application under 35 U.S.C. §371 of PCT Application No. PCT/EP2010/004298, filed Jul. 14, 2010, which claims the benefit of German application No. 20 2009 009 602.5 filed Jul. 15, 2009, the contents of each of which are expressly incorporated herein by reference.

FIELD OF ART

The present disclosure relates to a catheter device in which the needle retracted from the catheter is brought into a protective position inside a tubular receptacle.

BACKGROUND

EP 922 466 describes a catheter device of this kind wherein, in the ready position, the tubular receptacle for the needle engages a catheter hub via a projection at the distal end. A needle hub is displaceable inside the receptacle, and in the ready position this needle hub is impinged on by a spring and held in a distal position in the receptacle by a locking member. After the catheter has been inserted in a patient, the receptacle with the needle is withdrawn from the catheter hub, wherein the lock on the needle hub is released by the manually operated locking member, so that the needle hub is moved into a proximal position in the receptacle by the spring, in which position the needle tip is located in the protective position inside the receptacle, which at the distal side is provided with only a through hole for the passage of the needle.

From EP 1 240 916 it is known to provide in a catheter hub a valve member through which the needle extends in the ready position, and which automatically closes the catheter hub after retraction of the needle from the catheter hub such that no blood can emerge from the catheter hub. By means of a valve actuation member mounted displaceably in the catheter hub, the valve member can be re-opened when a syringe or an intravenous line is inserted in the catheter hub thereby displacing the valve actuating member into the open position.

SUMMARY

According to the present method, system and device, a needle which can be retracted into a receptacle is provided with a catheter device in whose catheter hub a valve member is disposed, which closes the catheter hub after removal of the needle and which can be brought into the open position when a syringe or intravenous line is inserted.

Further aims, advantages, features and possible applications of the present method, system and device become apparent from the following description of the embodiments with reference to the drawings.

Hereby, all the features described and/or shown diagrammatically form the subject matter of the present method, system and device, whether in themselves or in any meaningful combination, and independently of their summary in the claims and of the back-referencing of the claims.

BRIEF DESCRIPTION OF THE FIGURES

An exemplary embodiment of the present method, system and device is explained in more detail below with reference to the drawings, in which:

FIG. 1 shows a longitudinal section through a catheter device having a needle inserted therein in the ready position, FIG. 2 shows a view of the catheter device with the needle retracted and removed therefrom, FIG. 3 shows a syringe inserted in the catheter hub, FIG. 5 shows the embodiment of FIG. 4 during the retraction of the needle, and FIG. 6 shows the needle in the protective position.

DETAILED DESCRIPTION

Figure 4:
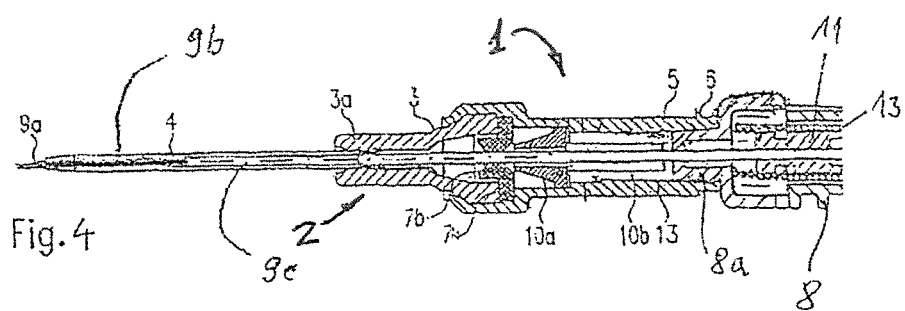
FIG. 4 shows an embodiment with a needle portion which supports sliding properties, in the ready position.

FIG. 1 shows a catheter insertion device 1 having a catheter hub 2, which is configured in two parts in the embodiment shown. A distal hub member 3 of the catheter hub has a holding portion 3a in which a catheter 4 is press-fitted by means of a funnel-shaped sleeve 3b. The proximal end of the hub member 3 has an enlarged diameter in relation to the distal end and forms a joining portion to a hub member 5, whose distal end engages the proximal end of the hub member 3 and which is provided at its proximal end with a Luer thread 6. Between the two hub members 3 and 5, a non-return valve is inserted in the form of a valve disc 7 which is fixed in its position by the two hub members 3 and 5. The catheter hub 2 can also be configured as one piece, wherein the valve disc 7 can be press-fitted therein.

In the ready position according to FIG. 1, there is inserted in the catheter hub 2 a receptacle 8 having a nose-shaped axially projecting boss 8a in which a hollow needle 9 is fixed in a needle hub 11. In the embodiment shown, the boss 8a is a separate piece, by means of which assembly is facilitated. It is also possible to mould the boss 8a on the receptacle 8 and to configure the proximal wall 8c as a cap or separate piece, by means of which assembly is facilitated. The needle 9 extends through the valve disc 7 and the catheter 4 so that the needle tip 9a is exposed. Between boss 8a and valve disc 7, a valve actuation member 10 is displaceably disposed in the proximal hub member 5 and has a truncated cone-shaped abutting portion 10a which serves to open the valve disc 7. On the proximal side, a push portion 10b is attached to the abutting portion 10a.

When the hollow needle 9 is retracted from the catheter hub 2, the valve disc 7, due to its resilience, closes the through hole for the hollow needle 9, as the separated position represented in FIG. 2 shows, so that no blood can emerge from the catheter 4. The silicon valve disc is provided, for example, with three slits starting from the middle and extending radially over a short portion to form resilient lugs 7b therebetween which can be widened by the hollow needle. Other embodiments of a valve are also possible, wherein a different number of slits can also be provided.

FIG. 3 shows a syringe 14 inserted in the catheter hub 2 and having a distally protruding luer taper 14a which is configured longer than the boss 8a at the receptacle 8, so that the valve actuating member 10 is displaced into the open position in FIG. 3.

The needle hub 11 is displaceably guided in the tubular receptacle 8 and held in the ready position in FIG. 1 by a locking member 12 against the force of a spring 13 which biases the needle hub 11 in the proximal direction. After the locking member 12 is released by pressure transverse to the receptacle 8, the needle hub 11 is displaced in the receptacle in a proximal direction by the spring 13.

FIGS. 4 and 5 show an embodiment in which a locking member 12 releasing the connection is not provided between the needle hub 11 and the receptacle 8. The spring-biased needle hub 11 is held in the ready position shown in FIG. 4 only by frictional force between the valve member 7 and the needle circumference and possibly by frictional force between the catheter tip 4a and the needle 9, wherein this frictional force is designed to be larger than the force of the spring 13. For this, the needle circumference can also be provided on the longitudinal portion 9c with a coating or surface treatment which increases the friction, to generate a correspond-ding frictional force between the valve member 7 and the needle circumference.

In addition or alternatively to this, the valve member 7 can be designed such that, for example, by means of lengthening the lugs 7b abutting at the needle circumference and corresponding surface treatment of the valve member, the frictional force between the needle circumference and the valve member 7 has the required strength, which is larger than the force of the spring 13 which impinges the needle hub 11 in the receptacle 8 in the proximal direction.

On a distal end portion 9b of the needle 9 in FIGS. 4 and 5, a coating or surface treatment is provided to reduce the friction between the needle circumference and the valve member 7 and between the catheter tip 4a and the needle 9, so that when the needle 9 is retracted from the catheter hub 5 (FIG. 5) a reduction in friction occurs between the uncoated area 9c of the needle 9 and the valve member 7 and the coated area 9b and valve member 7, by means of which the spring 13 is released. As soon as the portion 9b of the needle 9 which is provided with a sliding coating or corresponding surface treatment reaches the valve member 7, the force of the spring 13 becomes greater than the frictional force between this portion 9b of the needle circumference and the valve member 7, so that the holding effect in relation to the spring 13 is cancelled and the spring is released.

The needle can also have a uniform surface condition over its whole length, wherein the spring 13 only displaces the needle hub back into the receptacle 8 after the needle has been retracted through the narrowed tip 4a of the catheter 4 and there is no more additional frictional force between the needle 9 and the catheter tip 4a. The distal end portion 4a of a usual catheter 4 has a diameter which is slightly smaller than the outer diameter of the needle. On the remaining area, the catheter 4 is provided with an inner diameter which is larger than the outer diameter of the needle.

According to a further embodiment, a friction member (not shown) can be disposed in the catheter hub, preferably distally before the valve member 7, to exert a predetermined frictional force on the needle circumference so long as the friction member is acting on the needle circumference. When the needle 9 is retracted so far back that it is no longer impinged by the friction member, the friction force effecting the holding force for the spring 13 is reduced, so that the spring 13 moves the needle hub 11 into the proximal protective position in the receptacle 8.

Such a friction member can be provided in the catheter hub 2, either in addition to the embodiment of a low friction portion 9b or instead of the friction-reducing portion 9b of the needle.

Such a friction member can, for example, be a friction member which is impinged on by a radially acting spring and which presses onto the circumference of the needle 9 It is also possible to mount a friction member or friction members at the lugs 7b of the valve member 7, preferably on the distal side thereof, so that when the valve member 7 is opened by the valve actuating member 10, the friction members abutting at the needle circumference are moved out of the passage cross-section of the catheter hub when the syringe 14 is inserted (see FIG. 3).

An embodiment is also possible in which no valve actuating member 10 is provided in the catheter hub 2, but instead the valve member 7 is moved into the open position, for example, by positive pressure or negative pressure exerted by the syringe 14.

Furthermore, the receptacle 8 can be configured in a different way in connection with the needle hub 11 which is held only by frictional force in its ready position outside the receptacle 8. In FIG. 1, 8b designates vent openings for air to escape when the needle hub 11 is moved quickly by the spring 13 into the proximal protective position. Reference numeral 8c designates a cap. By way of example, the needle hub 11 can also be provided with a friction portion by means of which, in the ready position in FIG. 4, the holding force is maintained in connection with the frictional force in the catheter hub, whereupon on cessation of the frictional force in the catheter hub, the force of the spring 13 exceeds the frictional force of the needle hub 11 in the receptacle 8 and moves the needle hub into the protective position.

In FIG. 5, a distance between the catheter hub 2 and the receptacle 8 is represented which can only occur when the user holds the catheter hub 2 in one hand and also holds the receptacle 8 at a distance from the catheter hub 2 in the other hand. If the receptacle 8 is not held at a distance from the catheter hub 2, the spring 13 urges the receptacle 8 against the proximal end of the catheter hub. This has the advantage for the user that the needle portion 9c is covered while the needle is only partly retracted from the catheter hub 2 and, for example, the catheter hub 2 is fixed on the patient with adhesive tape. After this, the receptacle 8 can be retracted past the position represented in FIG. 5 until the spring 13 is released due to cessation of the frictional force in the catheter hub 2 and the needle is retracted in the receptacle 8.

The invention claimed is:

1. A catheter device comprising:
   a catheter hub in which a valve member is disposed;
   a needle fixed to a needle hub, the needle extending through the valve member in the catheter hub in a ready position; and
   a tubular receptacle in which the needle hub is displaceably guided and biased by a spring in a proximal direction relative to a distal end of the receptacle;
   wherein the needle hub is releasably held in the ready position in the receptacle against the force of the spring and the valve member is a valve disc comprising at least three slits forming resilient lugs.

2. The catheter device according to claim 1, wherein the needle hub is held in the receptacle by a manually operated locking member, against the force of the spring.

3. A catheter device comprising:
   a catheter hub in which a valve member is disposed;
   a needle fixed in a needle hub, the needle extending through the valve member in the catheter hub in a ready position;
   a tubular receptacle in which the needle hub is displaceably guided and biased by a spring in a proximal direction relative to a distal end of the receptacle;
   wherein the needle hub is releasably held in the ready position in the receptacle against the force of the spring; and
   wherein the needle hub is held in the ready position in the receptacle by frictional force between needle circumference and catheter or catheter hub, which frictional force is reduced on retraction of the needle through the catheter hub such that the force of the spring prevails.

4. The catheter device according to claim 3, wherein a member is provided in the catheter hub, generating a predetermined frictional force and exerting a predetermined frictional force on the needle circumference.

5. The catheter device according to claim 3, wherein a distal longitudinal portion of the needle circumference is provided with a friction-reducing coating or surface treatment, by means of which the distal longitudinal portion of the needle has a lower frictional force in relation to the friction member and/or the valve member than the remaining longitudinal portion of the needle.

6. The catheter device according to claim 3, wherein the spring urges the receptacle against the catheter hub and the receptacle covers the needle shaft when the needle is partly retracted from the catheter hub.

7. The catheter device according to claim 3, further comprising a valve actuator positioned inside the catheter hub and distal of the needle hub.

8. The catheter device according to claim 3, wherein the valve is a valve disc comprising at least three slits forming resilient lugs.

9. The catheter device according to claim 3, wherein the catheter hub comprises a distal hub portion attached to a proximal hub portion.

10. The catheter device according to claim 1, further comprising a valve actuator positioned inside the catheter hub and distal of an axially projecting boss.

11. The catheter device according to claim 1, wherein the catheter hub comprises a distal hub portion attached to a proximal hub portion.

12. The catheter device according to claim 10, wherein the valve actuator comprises a cone-shaped abutting portion for abutting the valve to open the valve.

13. The catheter device according to claim 1, wherein an axially projecting boss is a separate piece attached to the receptacle.

14. The catheter device according to claim 1, wherein an axially projecting boss is integrally formed with the receptacle.

15. A catheter device comprising:
a catheter hub in which a valve member is disposed;
a needle fixed to a needle hub, the needle extending through the valve member in the catheter hub in a ready position; and
a tubular receptacle in which the needle hub is displaceably guided and biased by a spring in a proximal direction relative to a distal end of the receptacle;
wherein the needle hub is releasably held in the ready position in the receptacle against the force of the spring; and
wherein the tubular receptacle has an axially projecting boss disposed distally of an end thereof and projecting inside the catheter hub.

16. A catheter device comprising:
a catheter hub in which a valve member is disposed;
a needle fixed to a needle hub, the needle extending through the valve member in the catheter hub in a ready position; and
a tubular receptacle in which the needle hub is displaceably guided and biased by a spring in a proximal direction relative to a distal end of the receptacle;
wherein the needle hub is releasably held in the ready position in the receptacle against the force of the spring; and
wherein the valve member has a plurality of slits that separate when the needle passes through the valve member and that separate when fluid flow is pushed through the catheter hub.

17. A catheter device comprising:
a catheter hub with a catheter tube in which a valve member having a least one slit is completely disposed; said catheter hub comprising an open proximal end for receiving a male implement to open at least one slit on the valve member;
a needle fixed to a needle hub, the needle extending through the valve member in the catheter hub and out a distal end of the catheter tube in a ready position;
a rigid tubular receptacle in which the needle hub is displaceably guided and biased by a spring in a proximal direction relative to the a distal end of the receptacle;
wherein the tubular receptacle has an axially projecting boss disposed distally of an end thereof and projecting inside the catheter hub,
wherein the needle hub is releasably held in the ready position in the receptacle against the force of the spring.

18. The catheter device of claim 17, further comprising a valve opener disposed inside the catheter hub and proximally of the valve member.

* * * * *

UNITED STATES PATENT AND TRADEMARK OFFICE
CERTIFICATE OF CORRECTION

PATENT NO.       : 8,728,030 B2  
APPLICATION NO.  : 13/381842  
DATED            : May 20, 2014  
INVENTOR(S)      : Kevin Woehr Page 1 of 1

It is certified that error appears in the above-identified patent and that said Letters Patent is hereby corrected as shown below:

On the title page item (74), column 2, line 1, delete "O'Neil" and insert -- O'Neill --, therefor.

In the Claims:

In column 5, line 12, claim 6, delete "shafi" and insert -- shaft --, therefor.

In column 6, line 26, claim 17, delete "a least" and insert -- at least --, therefor.

In column 6, line 35, claim 17, delete "the a" and insert -- a --, therefor.

Signed and Sealed this  
Twenty-first Day of October, 2014

Michelle K. Lee  
*Deputy Director of the United States Patent and Trademark Office*